United States Patent
Herzig et al.

Patent Number: 5,434,252
Date of Patent: Jul. 18, 1995

[54] REACTIVE DYES CONTAINING A 2,6-DIAMINOPYRIDINE COUPLING COMPONENT

[75] Inventors: Paul Herzig, Basel; Athanassios Tzikas, Pratteln; Anton Andreoli, Riehen; Claudia Carisch, Reinach, all of Switzerland

[73] Assignee: Ciba-Geigy Corporation, Ardsley, N.Y.

[21] Appl. No.: 328,599

[22] Filed: Oct. 25, 1994

Related U.S. Application Data

[63] Continuation of Ser. No. 94,639, Jul. 19, 1993, abandoned.

[30] Foreign Application Priority Data

Jul. 23, 1992 [CH] Switzerland .................. 2317/92

[51] Int. Cl.⁶ ............ C09B 62/085; C09B 67/22; D06P 1/382
[52] U.S. Cl. .................. 534/635; 8/549; 534/642
[58] Field of Search ............ 534/635, 642; 8/549

[56] References Cited

U.S. PATENT DOCUMENTS

| | | | |
|---|---|---|---|
| 4,033,943 | 7/1977 | Ramanathan et al. | 534/635 |
| 4,134,887 | 1/1979 | Fuchs et al. | 534/642 |
| 4,294,580 | 10/1981 | Henk et al. | 534/635 X |
| 4,473,499 | 9/1984 | Niwa et al. | 534/635 |
| 4,500,455 | 2/1985 | Niwa et al. | 534/635 |
| 4,515,716 | 5/1985 | Niwa | 534/635 |
| 5,003,052 | 3/1991 | Tzikas | 534/642 X |
| 5,106,960 | 4/1992 | Hurter et al. | 534/845 |

FOREIGN PATENT DOCUMENTS

| | | |
|---|---|---|
| 0043575 | 1/1982 | European Pat. Off. |
| 3227253 | 2/1983 | Germany |
| 1377505 | 12/1974 | United Kingdom |
| 1377506 | 12/1974 | United Kingdom |
| 1419330 | 12/1975 | United Kingdom |
| 2142926 | 1/1985 | United Kingdom ........ 534/635 |

*Primary Examiner*—Mary C. Lee
*Assistant Examiner*—Fiona T. Powers
*Attorney, Agent, or Firm*—Kevin T. Mansfield

[57] ABSTRACT

Reactive dyes of the formula

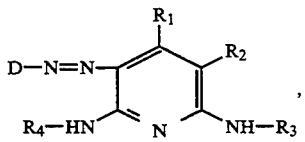

(1)

in which D, $R_1$, $R_2$, $R_3$ and $R_4$ are as defined in claim 1, are particularly suitable for dyeing or printing cellulosic fiber materials or naturally occurring or synthetic polyamide fiber materials with a high tinctorial yield, and produce dyeings and prints having good fastness properties.

9 Claims, No Drawings

REACTIVE DYES CONTAINING A 2,6-DIAMINOPYRIDINE COUPLING COMPONENT

This application is a continuation, of application Ser. No. 08/094,639, filed Jul. 19, 1993 now abandoned.

The present invention relates to novel reactive dyes, process for their preparation and their use for dyeing or printing fibre materials.

The practice of dyeing using reactive dyes has recently led to increased requirements on the quality of the dyeings and the economy of the dyeing process. Consequently, there continues to be a demand for novel reactive dyes which have improved properties, in particular in respect of application.

Reactive dyes which have an adequate substantivity and at the same time readily permit the non-fixed portions to be washed out are now required for dyeing. Furthermore, they should have a good tinctorial yield and a high reactivity, and dyeings with high degrees of fixing in particular should be produced. These requirements are not met in all their characteristics by the known dyes.

The present invention is therefore based on the object of discovering novel improved reactive dyes which can be used for dyeing and printing fibre materials and have the qualities characterised above to a high degree. In particular, the novel dye-stuffs should be distinguished by high fixing yields and high fibre-dye bond stabilities, and the portions not fixed on the fibre moreover should be easy to wash off. They should furthermore produce dyeings having good all-round properties, for example fastnesses to light and to wet conditions.

It has been found that the object described can be largely achieved using the novel reactive dyes defined below.

The invention therefore relates to reactive dyes of the formula

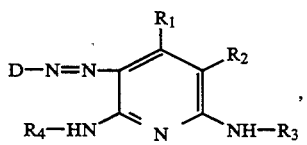
(1)

in which D is the radical of a diazo compound of the benzene or naphthalene series or the radical of a mono- or disazo dye, $R_1$ is $C_1$–$C_4$alkyl, $R_2$ is cyano, carbamoyl or sulfomethyl and $R_3$ and $R_4$ independently of one another are hydrogen or $C_1$–$C_{12}$alkyl which is unsubstituted or substituted and, with the exception of methyl, may be interrupted by oxygen, and the reactive dye of the formula (1) contains, as the fibre-reactive radical, a radical of the halotriazine series or halopyridimidine series or a radical of the formula —SO$_2$—Z, (2a)

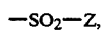
—W—alk—SO$_2$—Z, (2b)
R

—W—alk—E—alk'—SO$_2$—Z, (2c)

-continued

—alk—W—alk'—SO$_2$—Z, (2d)
R

—O—alk—W—alk'—SO$_2$—Z, (2e)
R

—W-arylene-N—alk—SO$_2$—Z or (2f)
R$_5$ R

—NH—CO—Z$_1$, (2g)

in which W is a group of the formula —SO$_2$—NR$_5$—, —CONR$_5$ or —NR$_5$CO—, $R_5$ is hydrogen, or $C_1$–$C_4$alkyl which is unsubstituted or substituted by hydroxyl, sulfo, sulfato, carboxyl or cyano, R is hydrogen, hydroxyl, sulfo, sulfato, carboxyl, cyano, halogen, $C_1$–$C_4$alkoxycarbonyl, $C_1$–$C_4$alkanoyloxy or carbamoyl, Z is a group of the formula —CH=CH$_2$ or —CH$_2$—CH$_2$—U$_1$ and U$_1$ is a leaving group, Z is a group of the

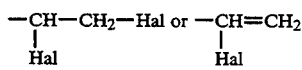

and Hal is halogen,

E is the radical —O— or —NR$_6$— and R$_6$ is hydrogen or $C_1$–$C_4$alkyl, alk and alk' independently of one another are $C_1$–$C_6$alkylene and arylene is a phenylene or naphthylene radical which is unsubstituted or substituted by sulfo, carboxyl, $C_1$–$C_4$alkyl, $C_1$–$C_4$alkoxy or halogen, the radical of the formula (2a) being bonded in the 2-position to a 5-sulfophenyl radical, and the reactive dye of the formula (1) contains at least one permanent sulfo or sulfato group and only one fibre-reactive radical.

Examples of substituents in the radical D are: alkyl groups having 1 to 12 carbon atoms, in particular 1 to 4 carbon atoms, such as methyl, ethyl, propyl, isopropyl or butyl, alkoxy groups having 1 to 8 carbon atoms, in particular 1 to 4 carbon atoms, such as methoxy, ethoxy, propoxy, isopropoxy or butoxy, alkanoylamino groups having 2 to 8 carbon atoms, in particular 2 to 4 carbon atoms, such as acetylamino or propionylamino, phenyl- or naphthylamino, alkoxycarbonylamino groups having 2 to 8 carbon atoms, in particular 2 to 4 carbon atoms, alkanoyl groups having 2 to 8 carbon atoms, in particular 2 to 4 carbon atoms, alkoxycarbonyl having 1 to 4 carbon atoms in the alkoxy radical, such as methoxycarbonyl or ethoxycarbonyl, alkylsulfonyl having 1 to 4 carbon atoms, such as methylsulfonyl or ethylsulfonyl, phenyl- or naphthylsulfonyl, alkoxycarbonyl having 1 to 4 carbon atoms in the alkoxy radical, such as methoxycarbonyl or ethoxycarbonyl, benzoyl, benzoylamino which is unsubstituted or substituted by $C_1$–$C_4$alkyl on the nitrogen, phenyl, naphthyl, amino, amino which is mono- or disubstituted by $C_1$–$C_{12}$alkyl, phenyl or naphthyl, trifluoromethyl, nitro, cyano, hydroxyl, halogen, such as fluorine, chlorine or bromine, carbamoyl, N-alkylcarbamoyl having 1 to 4 carbon atoms in the alkyl radical, such as N-methylcarbamoyl or N-ethylcarbamoyl, sulfamoyl, N-alkylsulfamoyl having 1 to 4 carbon atoms, such as N-methylsulfamoyl, N-ethylsulfamoyl, N-propylsulfamoyl, N-isopropylsulfamoyl or N-butylsulfamoyl, N-(β-hydroxyethyl)-sulfamoyl, N,N-di-(β-hydroxyethyl)-sulfamoyl, N-phenylsulfamoyl, ureido, carboxyl, sulfomethyl, sulfo or sulfato, and fibre-reactive radicals, it being possible for the substituents containing an alkyl, phenyl or naphthyl radical to be further substituted in the alkyl, phenyl or naphthyl radical, for example by the substituents defined above for D. The alkyl radicals furthermore can be interrupted by oxygen (—O—).

Fibre-reactive radicals are to be understood as meaning those which are capable of reacting with the hydroxyl groups of cellulose, the amino, carboxyl, hydroxyl and thiol groups of wool and silk or the amino and any carboxyl groups of synthetic polyamides to form covalent chemical bonds. The fibre-reactive radicals as a rule are bonded to the dye radical directly or via a bridge member. Suitable fibre-reactive radicals are, for example, those which contain at least one removable substituent on an aliphatic, aromatic or heterocyclic radical, or in which the radicals mentioned contain a radical suitable for reaction with the fibre material, for example a vinyl radical.

Permanent sulfo or sulfato groups are to be understood as meaning those which are not removed during reaction of the reactive dyes with the fibre material. The reactive dyes of the formula (1) preferably contain 1 to 5, in particular 1 to 3, permanent sulfo or sulfato groups.

The reactive dyes of the formula (1) contain only one fibre-reactive radical, which is bonded either to the radical D, to the radical $R_3$ or to the radical $R_4$.

Reactive radicals of the halotriazine series are, in particular, those of the formula

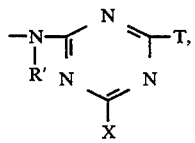 (3)

in which R' can be hydrogen or $C_1$-$C_{12}$alkyl which is unsubstituted or substituted and, with the exception of methyl, may be interrupted by oxygen and the radical —(NR')— can be a divalent 5- to 7-membered aliphatic heterocyclic radical, X is a group which can be removed as an anion and T is a group which can be removed as an anion or is a non-reactive radical.

Reactive radicals of the halopyrimidine series are, in particular, those of the formula

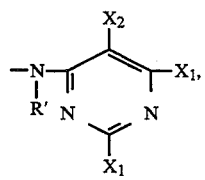 (4)

in which R' is as defined above, one of the radicals $X_1$ is a group which can be removed as an anion, the other radical $X_1$ is a group which can be removed as an anion or is a non-reactive substituent and $X_2$ is a negative substituent.

Examples of suitable leaving groups $U_1$ are —Cl, —Br, —F, —OSO$_3$H, —SSO$_3$H, —OCO—CH$_3$, —OPO$_3$H$_2$, —OCO—CCl$_3$, —OCO—CHCl$_2$, —O-CO—CH$_2$Cl, —OSO$_2$—$C_1$-$C_4$alkyl, —OSO$_2$—N(-$C_1$-$C_4$alkyl)$_2$ or —OCO—C$_6$H$_5$.

$U_1$ is preferably a group of the formula —Cl, —OSO$_3$H, —SSO$_3$H, —OCO—CH$_3$, —OCO—C$_6$H$_5$ or —OPO$_3$H$_2$, in particular —Cl or —OSO$_3$H, preferably —OSO$_3$H.

Alk and alk' independently of one another are, for example, a methylene, ethylene, 1,3-propylene, 1,4-butylene, 1,5-pentylene or 1,6-hexylene radical or branched isomers thereof.

Alk and alk' are preferably a $C_1$-$C_4$alkylene radical, and particularly preferably an ethylene radical.

Arylene is preferably a 1,3- or 1,4-phenylene radical, which is unsubstituted or, for example, substituted by sulfo, methyl, methoxy or carboxyl.

R is preferably hydrogen.

$R_5$ is preferably hydrogen or $C_1$-$C_4$alkyl, such as methyl, ethyl, propyl, isopropyl, butyl, isobutyl, sec-butyl or tert-butyl. $R_5$ is particularly preferably hydrogen.

E is preferably —NH— or —O—, and particularly preferably —O—.

W is preferably a group of the formula —CONH— or —NHCO—, in particular a group of the formula —CONH—.

Hal in the radical $Z_1$ is preferably chlorine or, in particular, bromine.

Preferred reactive radicals of the formulae (2a) to (2g) are those in which W is a group of the formula —CONH— or —NHCO—, R and $R_5$ are hydrogen, E is the radical —O— or —NH—, Hal is chlorine or bromine and $U_1$ is a group of the formula —Cl, —OSO$_3$H, —SSO$_3$H, —OCO—CH$_3$, —OCO—C$_6$H$_5$ or —OPO$_3$H$_2$, in particular a group of the formula —Cl or —OSO$_3$H.

R' is preferably hydrogen or $C_1$-$C_{12}$alkyl which is unsubstituted or substituted by hydroxyl, sulfo or sulfato and, with the exception of methyl, may be interrupted by oxygen, or the radical —(NR')— is a bivalent 5- to 7-membered aliphatic heterocyclic radical.

A 5- to 7-membered aliphatic heterocyclic radical —(NR')— is, in particular, the radical of the formula

The radical R' can be interrupted by oxygen, for example by 1 to 3, in particular 1 or 2 —O— radicals.

R' is preferably hydrogen or $C_1$-$C_{12}$alkyl, in particular $C_1$-$C_8$alkyl, which is unsubstituted or substituted by hydroxyl, sulfo or sulfato and, with the exception of methyl, may be interrupted by 1 to 3 —O— radicals, or the radical —(NR')— is a radical of the formula

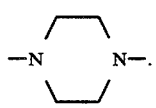

Examples of R' are methyl, ethyl, propyl, isopropyl, butyl, isobutyl, sec-butyl, tert-butyl or straight-chain or branched pentyl, hexyl or octyl, 2-hydroxyethyl, 3-hydroxypropyl, 2-sulfatoethyl, 3-sulfatopropyl, 2-sulfoethyl, 3-sulfopropyl, 2-methoxyethyl, 3-methoxypropyl and radicals of the formulae —(CH$_2$)$_2$—O—(CH$_2$)$_2$—OH and —(CH$_2$)$_2$—O—(CH$_2$)$_2$—OSO$_3$H.

R' is especially preferably hydrogen or C$_1$-C$_4$alkyl, in particular hydrogen, methyl or ethyl.

X is, for example, halogen, such as fluorine, chlorine or bromine, sulfo, C$_1$-C$_4$alkylsulfonyl or phenylsulfonyl, and preferably halogen, in particular fluorine or chlorine.

A group T which can be removed as an anion is, for example, halogen, such as fluorine, chlorine or bromine, sulfo, C$_1$-C$_4$alkylsulfonyl or phenylsulfonyl, and preferably halogen, in particular fluorine or chlorine.

A non-reactive substituent T can be, for example, hydroxyl, C$_1$-C$_4$alkoxy, C$_1$-C$_4$alkylthio, morpholino or unsubstituted or substituted amino.

T is preferably halogen, hydroxyl, sulfo, C$_1$-C$_4$alkoxy, C$_1$-C$_4$alkylthio, C$_1$-C$_4$alkylsulfonyl, phenylsulfonyl, morpholino or unsubstituted or substituted amino.

Unsubstituted or substituted amino T is unsubstituted amino or, for example, N-C$_1$-C$_4$alkylamino or N,N-di-C$_1$-C$_4$alkylamino, in which the alkyl is unsubstituted or substituted, for example, by sulfo, sulfato, hydroxyl, carboxyl or phenyl, cyclohexylamino, N-C$_1$-C$_4$alkyl-N-phenylamino or phenylamino or naphthylamino, in which the phenyl or naphthyl is unsubstituted or substituted, for example, by C$_1$-C$_4$alkyl, C$_1$-C$_4$alkoxy, C$_2$-C$_4$alkanoylamino, carboxyl, sulfo or halogen.

Examples of suitable non-reactive substituents T are amino, methylamino, ethylamino, β-hydroxyethylamino, N,N-di-β-hydroxyethylamino, β-sulfoethylamino, cyclohexylamino, morpholino, o-, m- or p-chlorophenylamino, o-, m- or p-methylphenylamino, o-, m- or p-methoxyphenylamino, o-, m- or p-sulfophenylamino, disulfophenylamino, o-carboxyphenylamino, 1- or 2-naphthylamino, 1-sulfo-2-naphthylamino, 4,8-disulfo-2-naphthylamino, N-ethyl-N-phenylamino, N-methyl-N-phenylamino, methoxy, ethoxy, n- or iso-propoxy and hydroxyl.

T is particularly preferably chlorine, fluorine, hydroxyl, sulfo, C$_1$-C$_4$alkoxy, C$_1$-C$_4$alkylthio, morpholino, amino, N-C$_1$-C$_4$alkylamino, which is unsubstituted in the alkyl part or substituted by hydroxyl, sulfato or sulfo, phenylamino or N-C$_1$-C$_4$alkyl-N-phenylamino, in which the phenyl in each case is unsubstituted or substituted by sulfo, carboxyl, acetylamino, methyl or methoxy.

T especially preferably is chlorine, fluorine, C$_1$-C$_4$alkoxy, morpholino, N-C$_1$-C$_4$alkyl-N-phenylamino or phenylamino, in which the phenyl in each case is unsubstituted or substituted by sulfo, carboxyl, acetylamino, methyl or methoxy, in particular sulfo.

A radical X$_1$ which can be removed as an anion is preferably halogen, in particular fluorine or chlorine.

A non-reactive substituent X$_1$ is as defined and preferred above, for example, for a non-reactive substituent T.

The radical X$_1$ is particularly preferably halogen, in particular fluorine or chlorine.

Examples of suitable radicals X$_2$ am nitro, cyano, C$_1$-C$_4$alkylsulfonyl, carboxyl, chlorine, hydroxyl, C$_1$-C$_4$alkoxysulfonyl, C$_1$-C$_4$alkylsulfinyl, C$_1$-C$_4$alkoxycarbonyl or C$_2$-C$_4$alkanoyl, preferably chlorine, cyano and methylsulfonyl for X$_2$·X$_2$ is particularly preferably halogen, in particular chlorine.

Preferred reactive radicals of the formula (3) are those in which X is halogen and T is halogen, hydroxyl, sulfo, C$_1$-C$_4$alkoxy, C$_1$-C$_4$alkylthio, C$_1$-C$_4$alkylsulfonyl, phenylsulfonyl, morpholino or unsubstituted or substituted amino, and wherein T is preferably as defined as preferred above.

Preferred reactive radicals of the formula (4) are those in which the two substituents X$_1$ are halogen, in particular chlorine or fluorine, and X$_2$ is halogen, in particular chlorine.

Particularly preferred reactive radicals of the formula (4) are those in which the two substituents X$_1$ are chlorine or fluorine and X$_2$ is chlorine.

The reactive dyes of the formula (1) preferably contain as fibre-reactive groups a reactive radical of the formulae (2a) to (2g) or a reactive radical of the formula (3) or (4) in which R' is hydrogen or C$_1$-C$_{12}$alkyl which is unsubstituted or substituted by hydroxyl, sulfo or sulfato and, with the exception of methyl, may be interrupted by oxygen, or the radical —(NR')— is a bivalent 5- to 7-membered aliphatic heterocyclic radical, X, X$_1$ and X$_2$ are halogen and T is halogen, hydroxyl, sulfo, C$_1$-C$_4$alkoxy, C$_1$-C$_4$alkylthio, C$_1$-C$_4$alkylsulfonyl, phenylsulfonyl, morpholino or unsubstituted or substituted amino, and the reactive radicals of the formulae (2a) to (2g), (3) and (4) are as defined and as preferred above.

C$_1$-C$_4$alkyl R$_1$ is methyl, ethyl, propyl, isopropyl, butyl, isobutyl, sec-butyl or tert-butyl, in particular methyl.

R$_2$ is preferably cyano or carbamoyl.

Substituents of the radicals R$_3$ and R$_4$ are, for example, hydroxyl, sulfo, sulfato, reactive radicals of the halotriazine or halopyrimidine series, in particular reactive radicals of the formulae (3) and (4) as defined above, and phenyl or naphthyl, in which the phenyl and naphthyl radicals are unsubstituted or further substituted by C$_1$-C$_4$alkyl, C$_1$-C$_4$alkoxy, C$_2$-C$_4$alkanoylamino, halogen or sulfo.

R$_3$ and R$_4$ independently of one another are preferably hydrogen, C$_1$-C$_{12}$alkyl which is unsubstituted or substituted by hydroxyl, sulfo or sulfato and, with the exception of methyl, may be interrupted by oxygen, or a radical of the formula

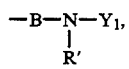

$$-B-N-Y_1, \quad (5)$$
$$\phantom{-B-N}|$$
$$\phantom{-B-N-}R'$$

in which R' is as defined and preferred above, B is C$_2$-C$_{12}$alkylene which is unsubstituted or substituted, in particular substituted by hydroxyl, sulfo or sulfato, and may be interrupted by oxygen, and Y$_1$ is a fibre-reactive radical of the halotriazine or halopyrimidine series, in particular a reactive radical of the formula

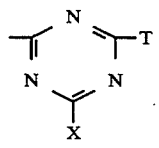

(6)

or

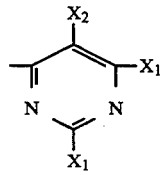

(7)

in which T, X, $X_1$ and $X_2$ are as defined and as preferred above.

The radicals $R_3$ and $R_4$ can thus be either non-reactive radicals or reactive radicals.

The radicals B, $R_3$ and $R_4$ can be interrupted by oxygen, for example by 1 to 3, in particular 1 or 2 —O— radicals.

The radical B is preferably $C_2$-$C_6$alkylene, which is unsubstituted or substituted by hydroxyl, sulfo or sulfato and may be interrupted by 1 to 3, in particular 1 or 2 —O— radicals.

The radical B is particularly preferably $C_2$-$C_6$alkylene, in particular 1,2-ethylene, 1,3-propylene or 1,6-hexylene.

Non-reactive radicals $R_3$ and $R_4$ are preferably hydrogen or $C_1$-$C_8$alkyl which is unsubstituted or substituted by hydroxyl, sulfo or sulfato and, with the exception of methyl, may be interrupted by 1 to 3, in particular 1 or 2, —O— radicals.

Examples of non-reactive radicals $R_3$ and $R_4$ are methyl, ethyl, propyl, isopropyl, butyl, isobutyl, sec-butyl, tert-butyl or straight-chain or branched pentyl, hexyl or octyl, 2-hydroxyethyl, 3-hydroxypropyl, 2-sulfatoethyl, 3-sulfatopropyl, 2-sulfoethyl, 3-sulfopropyl, 2-methoxyethyl, 3-methoxypropyl and radicals of the formulae —(CH$_2$)$_2$—O—(CH$_2$)$_2$—OH and —(CH$_2$)$_2$—O—(CH$_2$)$_2$—OSO$_3$H.

Preferred reactive radicals $R_3$ and $R_4$ are those of the formula (5) in which B and R' are as defined and as preferred above, X is halogen and T is halogen, hydroxyl, sulfo, $C_1$-$C_4$alkoxy, $C_1$-$C_4$alkylthio, $C_1$-$C_4$alkylsulfonyl, phenylsulfonyl, morpholino or unsubstituted or substituted amino, the two substituents $X_1$ are halogen, in particular chlorine or fluorine, and $X_2$ is halogen, in particular chlorine.

Very particularly preferred reactive radicals $R_3$ and $R_5$ are those of the formula (5) in which R' is hydrogen or $C_1$-$C_{12}$alkyl, in particular $C_1$-$C_8$alkyl, which is unsubstituted or substituted by hydroxyl, sulfo or sulfato and, with the exception of methyl, may be interrupted by 1 to 3 —O— radicals, or the radical —(NR')— is a radical of the formula

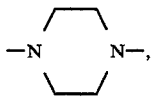

B is $C_2$-$C_8$alkylene which is unsubstituted or substituted by hydroxyl, sulfo or sulfato and may be interrupted by 1 to 3 —O— radicals, X is fluorine or chlorine, T is fluorine, chlorine, $C_1$-$C_4$alkoxy, morpholino, N—$C_1$-$C_4$alkyl-N-phenylamino or phenylamino, in which the phenyl in each case is unsubstituted or substituted by sulfo, carboxyl, acetylamino, methyl or methoxy, in particular sulfo, the two substituents $X_1$ are fluorine or chlorine and $X_2$ is chlorine.

The radical D is preferably a radical of the benzene or naphthalene series or the radical of a monoazo dye which contains a diazo component of the benzene or naphthalene series and a coupling component of the benzene or naphthalene series, in which the benzene and naphthalene radicals are unsubstituted or substituted by $C_1$-$C_4$alkyl, $C_1$-$C_4$alkoxy, $C_2$-$C_4$alkanoylamino, halogen, sulfo or a reactive radical of the formulae (2a) to (2g), (3) or (4).

Particularly preferred reactive dyes are those of the formulae

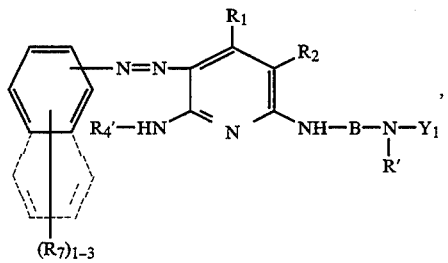

(8a)

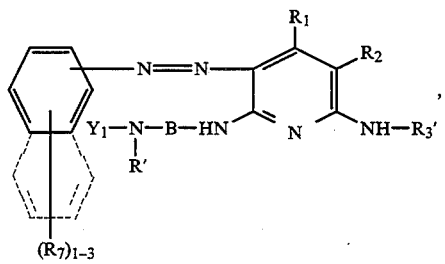

(8b)

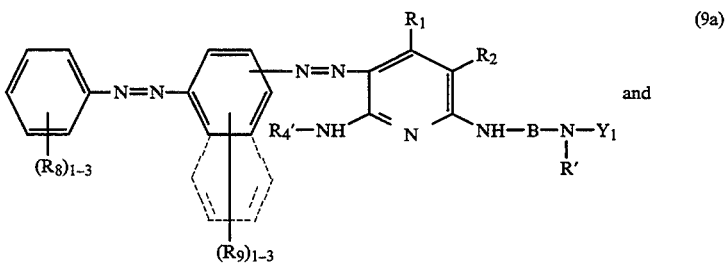

(9a)

and

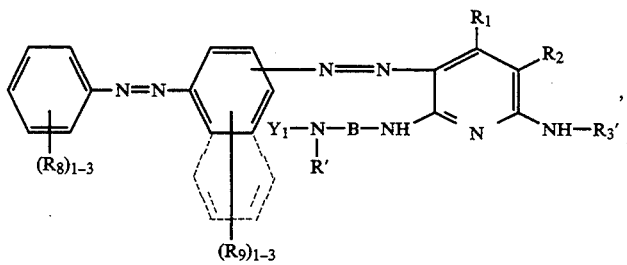

(9b)

in which $R_1$ is $C_1$-$C_4$alkyl, $R_2$ is cyano, carbamoyl or sulfomethyl, $R'$, $R_3'$ and $R_4'$ independently of one another are hydrogen or $C_1$-$C_{12}$alkyl which is unsubstituted or substituted by hydroxyl, sulfo or sulfato and, with the exception of methyl, may be interrupted by oxygen, the radical —(NR')— can be a divalent 5- to 7-membered aliphatic heterocyclic radical, $(R_7)_{1-3}$, $(R_8)_3$ and $(R_9)_{1-3}$ are in each case 1 to 3 identical or different substituents from the group comprising hydrogen, $C_1$-$C_4$alkyl, $C_1$-$C_4$alkoxy $C_2$-$C_4$alkanoylamino, halogen and sulfo, B is $C_2$-$C_{12}$alkylene which is unsubstituted or substituted by hydroxyl, sulfo and sulfato and may be interrupted by oxygen and $Y_1$ is a fibre-reactive radical of the formula (6) or (7).

Reactive dyes which are likewise particularly preferred are those of the formulae

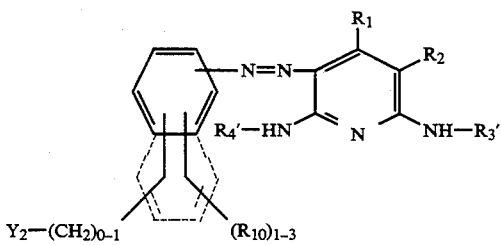

and

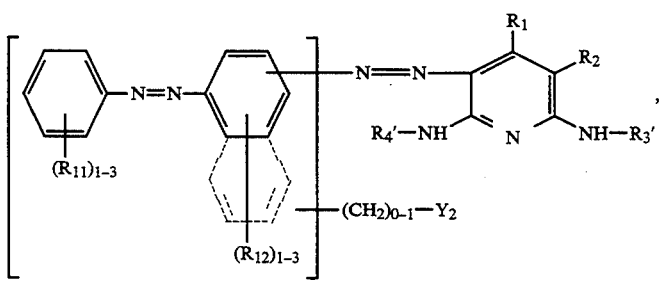

(11)

in which $R_1$ is $C_1$-$C_4$alkyl, $R_2$ is cyano, carbamoyl or sulfomethyl, $R_3'$ and $R_4'$ independently of one another are hydrogen or $C_1$-$C_{12}$alkyl which is unsubstituted or substituted by hydroxyl, sulfo or sulfato and, with the exception of methyl, may be interrupted by oxygen, $(R_{10})_{1-3}$, $(R_{11})_{1-3}$ and $(R_{12})_{1-3}$ in each case are 1 to 3 identical or different substituents from the group comprising hydrogen, $C_1$-$C_4$alkyl, $C_1$-$C_4$alkoxy, $C_2$-$C_4$alkanoylamino, halogen and sulfo and $Y_2$ is a fibre-reactive radical of the formulae (2a) to (2g), (3) or (4), in which, if $Y_2$ is a radical of the formula (2a), this is bonded in the 2-position to a 5-sulfophenyl radical.

The radicals $R_1$, $R_2$, $R'$, B, $Y_1$ of the formula (6) or (7) and $Y_2$ of the formulae (2a) to (2g), (3) or (4) are as defined and as preferred above. The radicals $R_3'$ and $R_4'$ are preferably the non-reactive radicals $R_3$ and $R_4$ as defined above as preferred.

Particularly preferred reactive radicals are those of the formulae (2b) to (2g), (3) and (4), in particular those of the formulae (2b), (2e), (2g), (3) and (4), and preferably those of the formulae (3) and (4).

Reactive groups of the formula (2a) are furthermore of interest. If the reactive dyes contain such a reactive radical, this is bonded in the 2-position to a 5-sulfophenyl radical. This means that the radical of the formula (2a) forms a radical of the formula

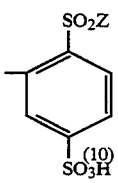

(10)

together with a structural element of the radical D. The radical D can be the radical of a diazo component of the benzene series or the radical of a mono- or disazo dye, and is otherwise preferably as defined as preferred above.

The invention furthermore relates to mixtures of reactive dyes which comprise at least two reactive dyes of the formula (1), the reactive dyes of the formula (1) being as defined and as preferred above.

Reactive dyes of the formula (1) in which $R_3$ and $R_4$ differ from one another are as a rule in the form of mixtures of two reactive dyes which differ merely in that the positions of the radicals $R_3$ and $R_4$ are interchanged. Particularly preferred mixtures are thus those which comprise a reactive dye of the formula $$D-N=N-\underset{R_4-HN}{\overset{R_1}{\underset{}{\bigvee}}}\underset{N}{\overset{R_2}{\underset{}{\bigvee}}}NH-R_3 \quad (1a)$$

and a reactive dye of the formula $$D-N=N-\underset{R_3-HN}{\overset{R_1}{\underset{}{\bigvee}}}\underset{N}{\overset{R_2}{\underset{}{\bigvee}}}NH-R_4 \quad (1b)$$

in which the reactive dyes of the formulae (1a) and (1b) differ only in that the positions of the radicals $R_3$ and $R_4$ are interchanged.

The present invention furthermore relates to a process for the preparation of the reactive dyes of the formula (1), which comprises diazotising an amine of the formula $$D-NH_2 \quad (12),$$

in which D is as defined under formula (1), and coupling the diazotisation product to a coupling component of the formula $$\underset{R_4-HN}{\overset{R_1}{\underset{}{\bigvee}}}\underset{N}{\overset{R_2}{\underset{}{\bigvee}}}NH-R_3 \quad (13)$$

in which $R_1$, $R_2$, $R_3$ and $R_4$ are as defined under formula (1), and if appropriate subsequently carrying out a further conversion reaction.

The diazotisation of the amine of the formula (12) is as a rule carried out by the action of nitrous acid in aqueous/mineral acid solution at a low temperature, for example 0° to 10° C., and the coupling to the coupling component of the formula (3) is carded out at an acid or neutral to weakly alkaline pH, in particular at a pH of 2 to 8.

A modified embodiment of the process comprises first preparing a dye which contains a precursor of the reactive radical and subsequently convening this into the final stage, for example by esterification or an addition reaction. For example, a dye in which Z is HO—CH$_2$CH$_2$— can be prepared and this product can be reacted with sulfuric acid such that the hydroxyl group is converted into the sulfato group. The sulfation of the hydroxyl group is carded out, for example, by reaction with concentrated sulfuric acid at about 0° C. to moderately elevated temperature.

The synthesis furthermore can be followed by elimination reactions. For example, reactive dyes of the formula (1) which contain sulfatoethylsulfonyl radicals can be treated with a base, for example sodium hydroxide, whereupon the sulfatoethylsulfonyl radicals are converted into vinylsulfonyl radicals.

In principle, the reactive dyes of the formula (1) can be prepared by starting from precursors or intermediates for dyes which contain fibre-reactive radicals, or these fibre-reactive radicals can be introduced into intermediate products which have a dye character and are suitable for this purpose.

Another interesting process for the preparation of reactive dyes of the formula (1) comprises subjecting a compound of the formula $$D-N=N-\underset{R_4-HN}{\overset{R_1}{\underset{}{\bigvee}}}\underset{N}{\overset{R_2}{\underset{}{\bigvee}}}NH-B-\underset{R'}{NH} \quad (14a)$$

or $$D-N=N-\underset{HN-B-HN}{\overset{R_1}{\underset{}{\bigvee}}}\underset{N}{\overset{R_2}{\underset{}{\bigvee}}}NH-R_3 \quad (14b)$$
$$\underset{R'}{|}$$

in which D, $R_1$, $R_2$, $R_3$ and $R_4$ are as defined under formula (1), R' is hydrogen or $C_1$-$C_{12}$alkyl which is unsubstituted or substituted and, with the exception of methyl, may be interrupted by oxygen, the radical —(NR')— can be a divalent 5- to 7-membered aliphatic heterocyclic radical and B is $C_2$-$C_{12}$alkylene which is unsubstituted or substituted and may be interrupted by oxygen, the compounds of the formulae (14a) and (14b) containing no fibre-reactive radical, to a condensation reaction with a fibre-reactive radical of the halotriazine or halopyrimidine series.

The condensation is as a rule carded out in aqueous solution at a temperature of, for example, 0° to 50° C. and a pH of, for example, 4 to 9.

The substituents of the compounds of the formula (12), (13), (14a) and (14b) are preferably as defined as preferred above.

Fibre-reactive radicals of the halotriazine or halopyrimidine series which can be subjected to a condensation reaction with the compounds of the formulae (14a) and (14b) are, in particular, radicals of the formulae $$\text{Hal}-\underset{N}{\overset{N}{\underset{}{\bigvee}}}\underset{X}{\overset{}{\bigvee}}-T \quad (15)$$

or $$\text{Hal}-\underset{N}{\overset{X_2}{\underset{}{\bigvee}}}\underset{X_1}{\overset{}{\bigvee}}-X_1, \quad (16)$$

in which Hal is halogen, in particular chlorine or fluorine, and T, X, X₁ and X₂ are as defined and as preferred above.

The compounds of the formulae (14a) and (14b) can be obtained by diazotisation of a corresponding amine of the formula (12) and coupling of the diazotisation product to a coupling component of the formula

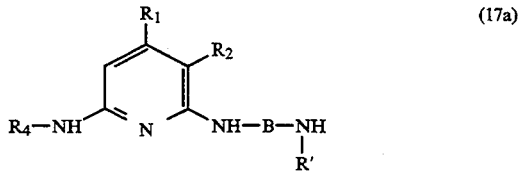 (17a)

or

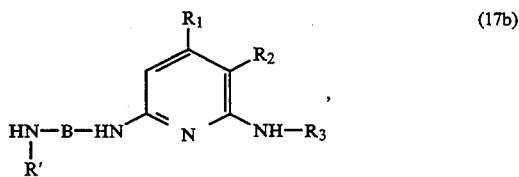 (17b)

by a procedure analogous to that described for the diazotisation of the amine of the formula (12) and the coupling to the coupling component of the formula (13).

The compounds of the formula (12), (13), (15) and (16) are known or can be prepared analogously to known compounds.

Some of the compounds of the formulae (17a) and (17b) are novel.

The present invention furthermore relates to the novel compounds of the formulae (17a) and (17b) in which $R_1$ is $C_1$-$C_4$alkyl, $R_2$ is cyano, carbamoyl or sulfomethyl, $R_3$, $R_4$ and $R'$ independently of one another are hydrogen or $C_1$-$C_{12}$alkyl which is unsubstituted or substituted and, with the exception of methyl, may be interrupted by oxygen, the radical —(NR′)— can be a divalent 5- to 7-membered aliphatic heterocyclic radical and B is $C_2$-$C_{12}$alkylene which is unsubstituted or substituted and may be interrupted by oxygen, with the proviso that if R′ is hydrogen, $R_3$ or $R_4$ are not 2-aminoethyl or 3-methoxypropyl.

The radicals $R_1$, $R_2$, $R_3$, $R_4$, R′ and B are preferably as defined as preferred above. Compounds of the formulae (17a) and (17b) in which R′ is not hydrogen are of interest.

As a rule, the compounds of the formulae (17a) and (17b) are in the form of mixtures, so that mixtures of the compounds of the formulae (17a) and (17b) are particularly preferred.

The present invention furthermore relates to a process for the preparation of the compounds of the formulae (17a) and (17b) which comprises reacting a compound of the formula

 (18)

with amines of the formulae $NH_2R_{13}$ and $NH_2$—B—NH—R′ (20)

and if appropriate subsequently carrying out a further conversion reaction, B, R′, $R_1$ and $R_2$ being as defined and $R_{13}$ being as defined for $R_3$ and $R_4$.

The reaction is carded out, for example, at a temperature of about 70° to 120° C., in particular 70° to 90° C., in a solvent, for example N,N-diethylaniline, triethylamine, higher alcohols or ketones, or the amines of the formulae (19) and (20) themselves are used as the solvent.

If mixtures of the amines of the formulae (19) and (20) are used and replacement of the chlorine atoms is complete, as a rule mixtures of the compounds of the formulae (17a) and (17b) are obtained.

By a suitable choice of reaction conditions, however, the chlorine atoms of the compound of the formula (18) can be replaced stepwise, which allows isolation of the individual mono- or disubstitution products.

Thus, in a first step, the chlorine atom in the para-position relative to the radical $R_2$ is chiefly removed at a lower temperature, for example 10° to 50° C., while the chlorine atom in the ortho-position relative to the radical $R_2$ is removed in a second step at a higher temperature, for example 70° to 120° C.

If the amines of the formulae (19) and (20) thus are added not together but in succession, either the compound of the formula (17a) or the compound of the formula (17b) can be obtained as the main product. It has proved advantageous here for the mono-substituted intermediate product obtained at a lower temperature in the first step to be isolated after the reaction and for the second step, the reaction of the second amine at a higher temperature, then to be carded out.

If the amine of the formula (19) is therefore added at a low temperature in the first step and the amine of the formula (20) is added at a higher temperature in the second step, the compound of the formula (17a) is obtained as the main compound. If the amines are employed in the reverse sequence, the compound of the formula (17b) is obtained as the main compound.

It has proved to be advantageous to employ the amine of the formula (20) in a large excess.

The dyes according to the invention of the formula (1) and the compounds of formulae (17a) and (17b) which contain sulfo or sulfato groups are present either in the form of their free acid or preferably as salts thereof.

Examples of suitable salts are the alkali metal salts, alkaline earth metal salts or ammonium salts or the salts of an organic amine. Examples are the sodium salts, lithium salts, potassium salts or ammonium salts or the salt of mono-, di- or triethanolamine.

The reactive dyes of the formula (1) are suitable for dyeing and printing widely varying materials, such as fibre materials containing hydroxyl groups or nitrogen. Examples are silk, leather, wool, polyamide fibres and polyurethanes, and in particular all types of cellulosic fibre materials. Such cellulosic fibre materials are, for example, the naturally occurring cellulosic fibres, such as cotton, linen and hemp, and cellulose and regenerated cellulose. The reactive dyes of the formula (1) are also suitable for dyeing or printing fibres containing hydroxyl groups which are contained in blend fabrics, for example blends of cotton with polyester fibres or polyamide fibres. The reactive dyes of the formula (1) are particularly suitable for dyeing or printing cellulosic fibre materials or, in particular, naturally occurring or synthetic polyamide fibre materials.

The dyes according to the invention can be applied to the fibre material and fixed to the fibre in various ways, in particular in the form of aqueous dye solutions and printing pastes. They are suitable both for the exhaust process and for dyeing by the pad-dyeing process, in which the goods are impregnated with aqueous dye solutions, which contain salts if appropriate, and the dyes are fixed, after treatment with an alkali or in the presence of an alkali and if appropriate with the action of heat. They are particularly suitable for the so-called cold pad-batch process, in which the dye is applied on the padder together with the alkali and, after storing at room temperature for several hours, is then fixed. After fixing, the dyes or prints are rinsed thoroughly with cold and hot water, if appropriate with the addition of a dispersing agent which promotes diffusion of the non-fixed portions.

The reactive dyes of the formula (1) are distinguished by a high reactivity, good fixing capacity and a very good build-up capacity. They can therefore be employed by the exhaust dyeing process at low dyeing temperatures, and require only short steaming times in the pad-steam process. The degrees of fixing are high and the non-fixed portions can easily be washed off, the difference between the degree of exhaustion and degree of fixing being remarkably low, i.e. the soaping loss is very low. The reactive dyes of the formula (1) are also particularly suitable for printing, in particular on cotton, but also for printing on nitrogen-containing fibres, for example wool or silk or blend fabrics containing wool or silk.

The dyeings and prints produced with the dyes according to the invention have a high colour strength and a high fibre-dye bond stability both in the acid and in the alkaline range, and furthermore a good light-fastness and very good wet-fastness properties, such as fastnesses to washing, water, sea-water, crossdyeing and perspiration, as well as a good fastness to pleating, ironing and rubbing.

The following examples serve to illustrate the invention. The temperatures are in degrees Celcius and parts and percentages are by weight, unless stated otherwise. Parts by weight bear the same relation to parts by volume as the kilogram to the liter.

Example 1

187 parts of 2,6-dichloro-3-cyano-4-methylpyridine are introduced into 427 parts of ethanolamine at a temperature of 20° to 30° C. The mixture is stirred at 20° to 30° C. for 2 hours. The clear brown solution is poured onto 3000 parts of ice-water. The precipitate formed is filtered off, washed with water and dried.

180 parts of a mixture of the compounds of the formulae

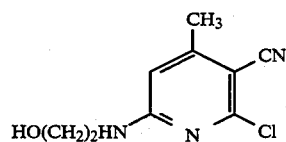

(101)

and

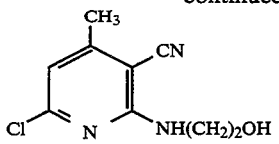

(102)

are obtained, the ratio of the compound of the formula (101) to the compound of the formula (102) being 3:1.

180 parts of the mixture of the compounds of the formulae (101) and (102) obtained as described are introduced into 630 parts of 1,3-diaminopropane at a temperature of 100° C. The mixture is subsequently stirred at a temperature of 100° C. for one hour. 45 parts of sodium carbonate are sprinkled into the clear solution at this temperature. The excess 1,3-diaminopropane is distilled off under a reduced vacuum. 500 parts of water are added to the residue and the organic phase is separated off at room temperature. For crystallisation, the organic phase is dissolved in 600 parts of isopropanol and the solution is acidified with 85 parts of hydrochloric acid (37%). The mixture is stirred at a temperature of 0° to 5° C. and the resulting precipitate is filtered off. After drying, 125 parts of a mixture of the compounds of the formulae

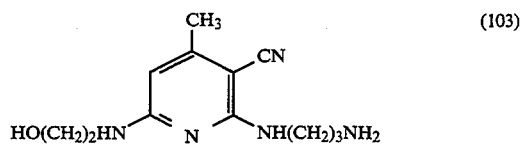

(103)

and

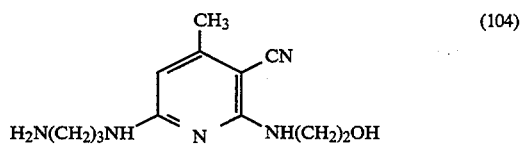

(104)

are obtained, the ratio of the compound of the formula (103) to the compound of the formula (104) being 3:1.

Example 2

187 pans of 2,6-dichloro-3-cyano-4-methylpyridine are introduced into 630 parts of 1,3-diaminopropane at a temperature of 20° to 30° C. The mixture is stirred at 20° to 30° C. for 2 hours.

The brown suspension is filtered and the residue is washed with ice-water and dried. 150 parts of a mixture comprising about 75% of

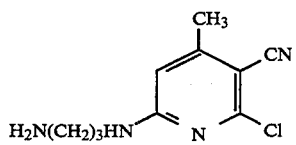

and about 25% of

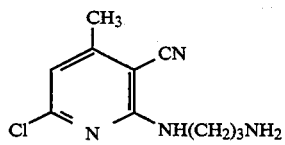

is obtained.

150 parts of the above mixture are introduced into 427 parts of ethanolamine at 100° C. The mixture is subsequently stirred at 100°–110° C. for 1 hour. 45 parts of sodium carbonate are sprinkled onto the clear brown solution. The excess ethanolamine is distilled off in vacuo, 500 parts of water are added to the residue and the organic phase is separated off at room temperature. For crystallisation, the organic phase is dissolved in 600 parts of isopropanol and the solution is acidified with 85 parts of 37% hydrochloric acid. The mixture is stirred at 0° to 5° C. and the resulting precipitate is filtered off. After drying, 110 parts of a mixture of about 75% of

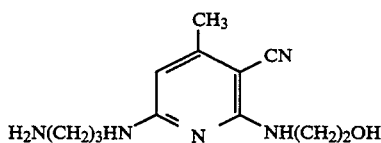

and about 25% of

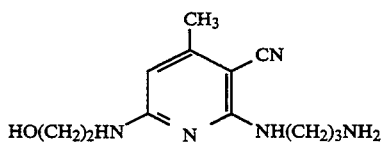

are obtained.

Examples 3 to 50

Mixtures of 2,6-diaminopyridine compounds which comprise the 2,6-diaminopyridine compounds shown in column 2 in the following Table 1 as the main component can be obtained analogously to Example 1. The components of the mixtures differ only in that the definitions of the amino radicals in the 2- and 6-position are interchanged.

TABLE 1

| Example | 2,6-Diaminopyridine compound |
|---|---|
| 3 | HO(CH₂)₂HN—[pyridine, CH₃, CN]—NH(CH₂)₂NH₂ |
| 4 | HO(CH₂)₂HN—[pyridine, CH₃, CN]—NH(CH₂)₆NH₂ |
| 5 | HO(CH₂)₂HN—[pyridine, CH₃, CN]—NH(CH₂)₃O(CH₂)₄O(CH₂)₃NH₂ |
| 6 | HO(CH₂)₂HN—[pyridine, CH₃, CN]—NH(CH₂)₂O(CH₂)₂NH₂ |

TABLE 1-continued

| Example | 2,6-Diaminopyridine compound |
|---|---|
| 7 | HO(CH₂)₂HN—[pyridine, CH₃, CN]—NH(CH₂)₂NH(CH₂)₂OH |
| 8 | HO(CH₂)₂HN—[pyridine, CH₃, CN]—NH(CH₂)₂NHC₂H₅ |
| 9 | HO(CH₂)₂HN—[pyridine, CH₃, CN]—NHCH₂CHCH₂NH₂ with OH |
| 10 | HO(CH₂)₂HN—[pyridine, CH₃, CN]—NH(CH₂)₂—N(piperazine)NH |
| 11 | HO₃SO(CH₂)₂HN—[pyridine, CH₃, CN]—NH(CH₂)₃NH₂ |
| 12 | HO₃SO(CH₂)₂HN—[pyridine, CH₃, CN]—NH(CH₂)₂NH₂ |
| 13 | HO₃SO(CH₂)₂HN—[pyridine, CH₃, CN]—NH(CH₂)₂O(CH₂)₂NH₂ |
| 14 | HO(CH₂)₂HN—[pyridine, CH₃, CN]—NHCH₂CHCH₂NH₂ with OSO₃H |
| 15 | HO₃SO(CH₂)₃HN—[pyridine, CH₃, CN]—NH(CH₂)₃NH₂ |
| 16 | HO₃SO(CH₂)₃HN—[pyridine, CH₃, CN]—NH(CH₂)₂NH(CH₂)₂OSO₃H |

TABLE 1-continued

| Example | 2,6-Diaminopyridine compound |
|---|---|
| 17 | 4-methyl-3-cyano-6-[HO(CH₂)₃HN]-2-[NH(CH₂)₃NH₂]-pyridine |
| 18 | 4-methyl-3-cyano-6-[HO(CH₂)₃HN]-2-[NH(CH₂)₃O(CH₂)₄O(CH₂)₃NH₂]-pyridine |
| 19 | 4-methyl-3-cyano-6-[HO(CH₂)₂O(CH₂)₂HN]-2-[NH(CH₂)₃NH₂]-pyridine |
| 20 | 4-methyl-3-cyano-6-[HO₃S(CH₂)₂HN]-2-[NH(CH₂)₆NH₂]-pyridine |
| 21 | 4-methyl-3-cyano-6-[H₃CO(CH₂)₂HN]-2-[NH(CH₂)₂NH₂]-pyridine |
| 22 | 4-methyl-3-cyano-6-[H₃C(CH₂)₃HN]-2-[NH(CH₂)₆NH₂]-pyridine |
| 23 | 4-methyl-3-cyano-6-[H₃C(CH₂)₂HN]-2-[NH(CH₂)₂NH₂]-pyridine |
| 24 | 4-methyl-3-cyano-6-[H₃C(CH₂)₄HN]-2-[NH(CH₂)₂NH₂]-pyridine |
| 25 | 4-methyl-3-carbamoyl-6-[HO(CH₂)₂HN]-2-[NH(CH₂)₃NH₂]-pyridine |
| 26 | 4-methyl-3-carbamoyl-6-[HO₃SO(CH₂)₂HN]-2-[NH(CH₂)₃NH₂]-pyridine |
| 27 | 4-methyl-3-carbamoyl-6-[HO₃S(CH₂)₂HN]-2-[NH(CH₂)₃NH₂]-pyridine |
| 28 | 4-methyl-3-carbamoyl-6-[HO(CH₂)₃HN]-2-[NH(CH₂)₃NH₂]-pyridine |
| 29 | 4-methyl-3-carbamoyl-6-[HO(CH₂)₃HN]-2-[NH(CH₂)₂NH₂]-pyridine |
| 30 | 4-methyl-3-carbamoyl-6-[HO(CH₂)₂HN]-2-[NH(CH₂)₂NH₂]-pyridine |
| 31 | 4-methyl-3-carbamoyl-6-[HO₃SO(CH₂)₃HN]-2-[NH(CH₂)₆NH₂]-pyridine |
| 32 | 4-methyl-3-carbamoyl-6-[HO₃SO(CH₂)₃HN]-2-[NH(CH₂)₂NH₂]-pyridine |
| 33 | 4-methyl-3-carbamoyl-6-[HO(CH₂)₂O(CH₂)₂HN]-2-[NH(CH₂)₃NH₂]-pyridine |
| 34 | 4-methyl-3-carbamoyl-6-[HO₃SO(CH₂)₂O(CH₂)₂HN]-2-[NH(CH₂)₃NH₂]-pyridine |
| 35 | 4-methyl-3-carbamoyl-6-[H₃C(CH₂)₃HN]-2-[NH(CH₂)₂O(CH₂)₂NH₂]-pyridine |
| 36 | 4-methyl-3-carbamoyl-6-[H₃CO(CH₂)₂HN]-2-[NHCH₂CH(OSO₃H)CH₂NH₂]-pyridine |

TABLE 1-continued

| Example | 2,6-Diaminopyridine compound |
|---|---|
| 37 | HO(CH₂)₂HN—[4-CH₃, 3-CONH₂ pyridine]—NH(CH₂)₃O(CH₂)₄O(CH₂)₃NH₂ |
| 38 | (CH₃)₂CHHN—[4-CH₃, 3-CN pyridine]—NH(CH₂)₃NH₂ |
| 39 | HO(CH₂)₂HN—[4-CH₃, 3-CN pyridine]—NH(CH₂)₄NH₂ |
| 40 | HO₃SO(CH₂)₂HN—[4-CH₃, 3-CONH₂ pyridine]—NH(CH₂)₂NH(CH₂)₂OSO₃H |
| 41 | HO₃SO(CH₂)₂HN—[4-CH₃, 3-CONH₂ pyridine]—NH(CH₂)₂NH₂ |
| 42 | HO₃SO(CH₂)₃HN—[4-CH₃, 3-CN pyridine]—NH(CH₂)₄NH₂ |
| 43 | HO₃S(CH₂)₂HN—[4-CH₃, 3-CN pyridine]—NH(CH₂)₂NH₂ |
| 44 | H₃C(CH₂)₂HN—[4-CH₃, 3-CONH₂ pyridine]—NH(CH₂)₄NH₂ |
| 45 | HO(CH₂)₃HN—[4-CH₃, 3-CN pyridine]—NH(CH₂)₄NH₂ |
| 46 | H₃CO(CH₂)₂HN—[4-CH₃, 3-CONH₂ pyridine]—NH(CH₂)₂NH₂ |
| 47 | H₃CCH₂HN—[4-CH₃, 3-CN pyridine]—NH(CH₂)₂NH₂ |
| 48 | CH₃(CH₂)₄HN—[4-CH₃, 3-CONH₂ pyridine]—NH(CH₂)₂NH₂ |
| 49 | HO₃SO(CH₂)₂HN—[4-CH₃, 3-CN pyridine]—NH(CH₂)₄NH₂ |
| 50 | H₃C(CH₂)₄HN—[4-CH₃, 3-CN pyridine]—NH(CH₂)₄NH₂ |

Example 51

28 pans of aniline-2-p-sulfatoethylsulfonyl-5-sulfonic acid in 300 pans of an ice-water suspension are acidified with 18 parts of concentrated aqueous hydrochloric acid and diazotised with 15.6 parts of a 5 normal sodium nitrite solution. The mixture is subsequently stirred at a temperature of about 5° C. for one hour, and excess nitrous acid is then destroyed by means of amidosulfonic acid. The diazonium salt solution thus prepared is allowed to run slowly into a suspension of 12 parts of the coupling component of the formula

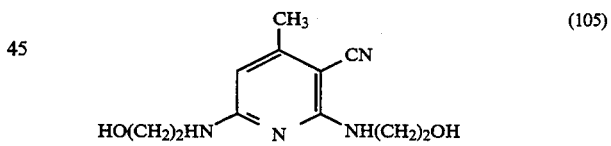
(105)

in 100 parts of water at a pH of 4 to 5. The pH is increased to a value of 6 to 7 by addition of sodium bicarbonate. The mixture is subsequently stirred for 2 hours until coupling is complete. The dye is then subjected to reverse osmosis and freeze dried. A dye is obtained which, in the form of the free acid, is the compound of the formula

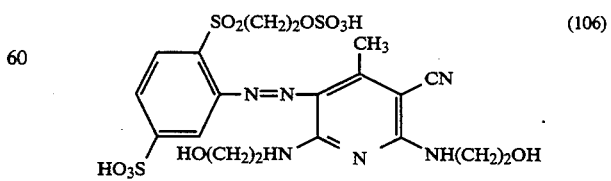
(106)

The dye of the formula (106) dyes cotton and wool in brilliant orange shades.

Example 52

22 parts of 5-(2',3'-dibromopropionamido)aniline-2-sulfonic acid in 280 parts of an ice-water suspension are acidified with 18 parts of concentrated aqueous hydrochloric acid and diazotised with 15.6 parts of a 5-normal sodium nitrite solution. The mixture is subsequently stirred at a temperature of about 5° to 15° C. for one hour and excess nitrous acid is then destroyed by means of amidosulfonic acid. The diazonium salt solution thus prepared is allowed to run slowly into a suspension of 12 parts of the coupling component of the formula (105) in 100 parts of water at a pH of 4 to 5. The pH is increased to a value of 6 to 7 by addition of sodium bicarbonate. The mixture is subsequently stirred for 2 hours until coupling is complete. The dye is then subjected to reverse osmosis and freeze dried. A dye is obtained which, in the form of the free acid, is the compound of the formula

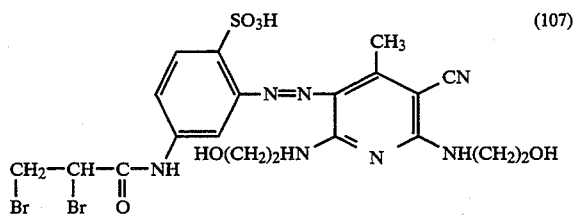

The dye of the formula (107) dyes cotton and wool in brilliant yellow shades.

Example 53

22 parts of 4-(2',3'-dibromopropionamido)aniline-2-sulfonic acid in 300 parts of an ice-water suspension are acidified with 18 parts of concentrated aqueous hydrochloric acid and diazotised with 15.6 parts of a 5-normal sodium nitrite solution. The mixture is subsequently stirred at a temperature of about 5° to 15° C. for one hour and excess nitrous acid is then destroyed by means of amidosulfonic acid. The diazonium salt solution thus prepared is allowed to run slowly into a suspension of 12 parts of the coupling component of the formula (105) in 100 parts of water at a pH of 4 to 5. The pH is increased to a value of 6 to 7 by addition of sodium bicarbonate. The mixture is subsequently stirred for 2 hours until coupling is complete. The dye is then subjected to reverse osmosis and freeze dried. A dye is obtained which, in the form of the free acid, is the compound of the formula

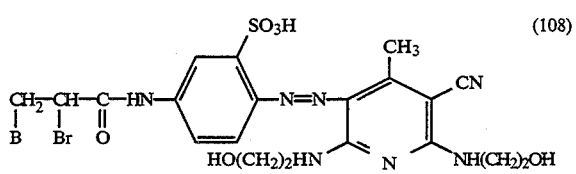

The dye of the formula (108) dyes cotton and wool in brilliant orange shades.

Example 54

25.3 parts of aniline-2,5-disulfonic acid are dissolved in 90 parts of water by addition of sodium carbonate solution to a pH of 4. 14 parts of cyanuric fluoride are uniformly added dropwise to the solution at a temperature of 0° to 5° C. in the course of 10 minutes, the pH is kept at 4 to 4.5 by addition of further sodium carbonate solution, the mixture is then subsequently stirred for 15 minutes and the pH is then adjusted to 5.5.

A solution of 300 parts of water and 46 parts of a mixture of the compound of the formulae

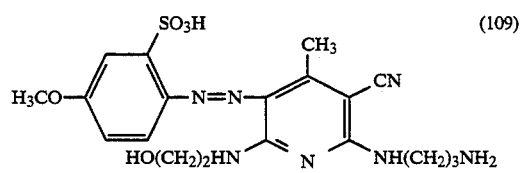

and

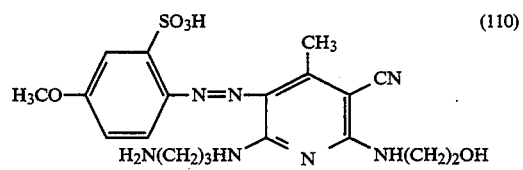

is then allowed to run into this solution and a condensation reaction is carried out at room temperature and at a pH of 5.5 to 8. After the condensation, the solution is subjected to reverse osmosis and freeze dried. 80 parts of a mixture are obtained which comprises the dyes, shown in the form of the free acids, of the formulae

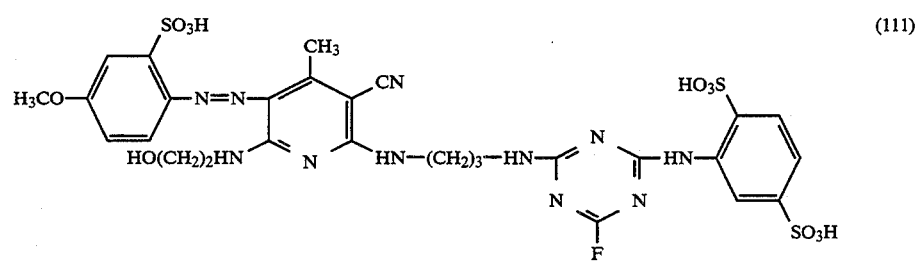

and

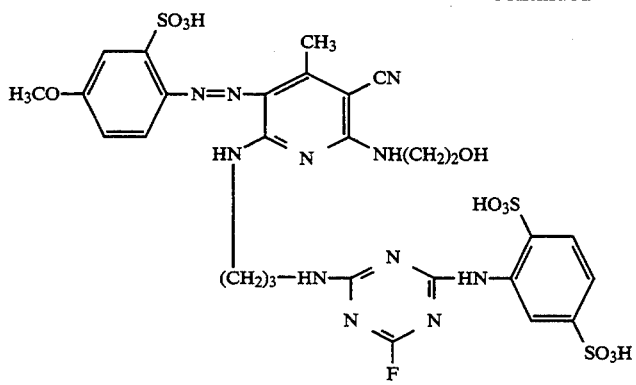

(112)

the dye of the formula (111) being the main component.

The mixture of dyes of the formulae (111) and (112) dyes cotton and wool in brilliant orange shades.

The mixture of compounds of the formulae (109) and (110) can be prepared by diazotisation of 2-sulfo-4-methoxyaniline (by acidification with hydrochloric acid and addition of sodium nitrite) and subsequent coupling to a mixture of the compounds of the formulae (103) and (104) obtainable according to Example 1.

Example 55

25.3 parts of aniline-2,5-disulfonic acid in 300 parts of an ice-water suspension are dissolved by addition of a sodium bicarbonate solution to a pH of 4. A solution of 19 parts of cyanuric chloride in acetone is allowed to run into the solution in the course of 30 minutes and the pH is kept at 4 to 4.5 by addition of further sodium bicarbonate solution. When the condensation reaction is complete, when no further free amine is detectable by a diazotisation sample, a solution of 18.8 parts of 1,3-phenylenediamine-4-sulfonic acid and 200 parts of water is added at a pH of 4 to 5. The mixture is then subsequently stirred at room temperature and at a pH of 4 to 5 for 3 hours. The solution thus obtained contains the compound which, in the form of the free acid, has the formula

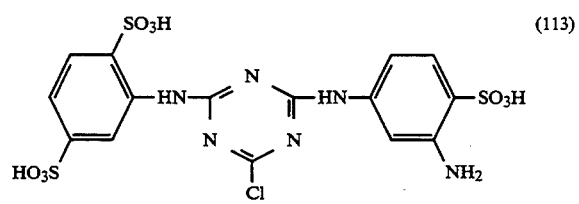

(113)

The solution containing the compound of the formula (113) is diazotised in the customary manner (by acidification with hydrochloric acid and addition of sodium nitrite) and the diazotisation product is coupled to a suspension of 200 parts of water and 24 pans of a coupling component of the formula

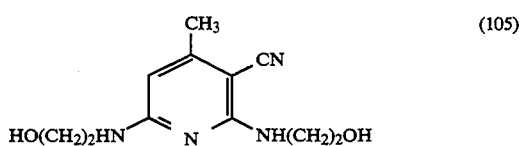

(105)

at a temperature of 0° to 5° C. and at a pH of 5 to 8. After the coupling, the reaction mass is subjected to reverse osmosis and freeze dried. A dye is obtained which, in the form of the free acid, is the compound of the formula

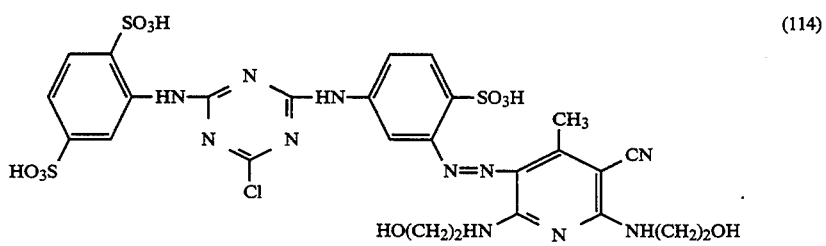

(114)

The dye of the formula (114) dyes cotton and wool in brilliant golden yellow shades.

Examples 56 to 129

The reactive dyes shown in the form of the free acids in Table 2 can be obtained analogously to Examples 51 to 55. If the reactive dyes shown in Table 2 contain a 2,6-diaminopyridine radical in which the amino radicals bonded in the 2- and 6-position differ from one another, mixtures of reactive dyes which comprise the reactive dyes shown in column 2 in the following Table 2 as the main component are obtained. The components of the mixtures differ only in that the definitions of the amino radicals in the 2- and 6-position of the 2,6-diaminopyridine radical are interchanged. The reactive dyes and reactive dye mixtures shown in column 2 dye cotton and wool in the colour shades shown in column 3.

TABLE 2

| Example | Reactive dye | Colour shade |
|---|---|---|
| 56 | Structure with SO₃H, HO₃SO(CH₂)₂SO₂(CH₂)₂NHOC-phenyl-N=N-pyridine(CH₃)(CONH₂) with HO(CH₂)₃HN and NH(CH₂)₂O(CH₂)₂OH substituents | Yellow |
| 57 | Structure with SO₂(CH₂)₂OSO₃H, HO₃S-phenyl-N=N-pyridine(CH₃)(CN) with HO(CH₂)₂O(CH₂)₂HN and NH(CH₂)₂O(CH₂)₂OH substituents | Orange |
| 58 | Structure with SO₂(CH₂)₂OSO₃H, HO₃S-phenyl-N=N-pyridine(CH₃)(CN) with HO(CH₂)₂HN and NH(CH₂)₂OCH₃ substituents | Orange |
| 59 | Structure: HO₃SO(CH₂)₂SO₂(CH₂)₂NHOC-phenyl-N=N-pyridine(CH₃)(CONH₂) with HO₃SO(CH₂)₂HN and NH(CH₂)₃OSO₃H substituents | Yellow |
| 60 | Structure: HO₃SO(CH₂)₂SO₂(CH₂)₃NHOC-phenyl-N=N-pyridine(CH₃)(CONH₂) with HO₃SO(CH₂)₂HN and NH(CH₂)₃OSO₃H substituents | Yellow |
| 61 | Structure: HO₃SO(CH₂)₂SO₂(CH₂)₃NHOC-phenyl-N=N-pyridine(CH₃)(CONH₂) with HO₃SO(CH₂)₂HN and NH(CH₂)₃OSO₃H substituents | Yellow |
| 62 | Structure: HO₃S(CH₂)₂SO₂(CH₃)₂HNOCCH₂O-phenyl(HO₃S)-N=N-pyridine(CH₃)(CN) with HO(CH₂)₂HN and NH(CH₂)₂OH substituents | Orange |
| 63 | Naphthalene structure with SO₃H, H₂C=CBrOCHNCH₂, -N=N-pyridine(CH₃)(CONH₂) with HO₃SO(CH₂)₂HN and NH(CH₂)₄CH₃ substituents | Orange |
| 64 | Structure with SO₂(CH₂)₂OSO₃H, HO₃S-phenyl-N=N-phenyl-N=N-pyridine(CH₃)(CONH₂) with HO₃SO(CH₂)₂HN and NH(CH₂)₂OSO₃H substituents | Orange |

TABLE 2-continued
| Example | Reactive dye | Colour shade |
|---|---|---|
| 65 | 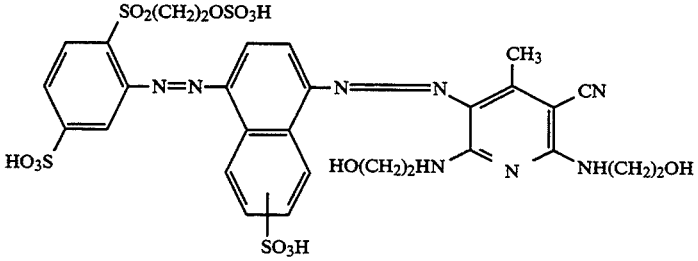 | Orange |
| 66 | 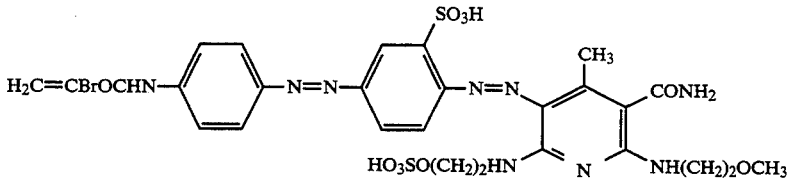 | Red |
| 67 | 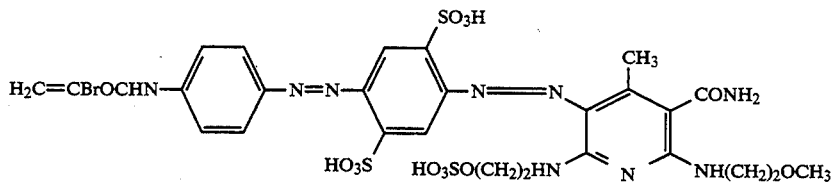 | Red |
| 68 | 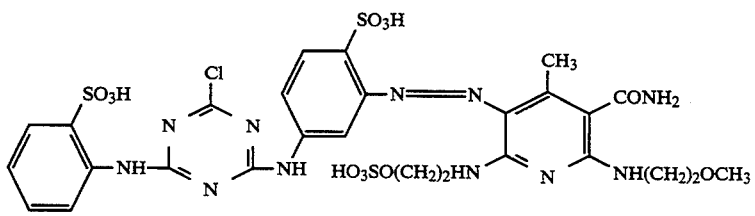 | Yellow |
| 69 | 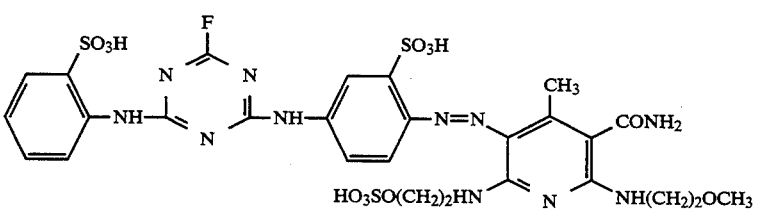 | Orange |
| 70 | 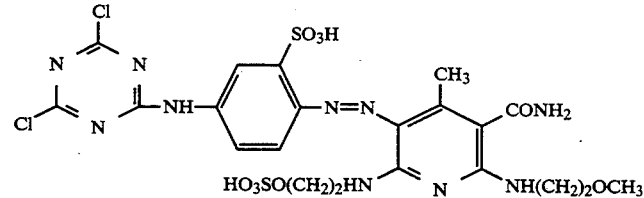 | Orange |
| 71 | 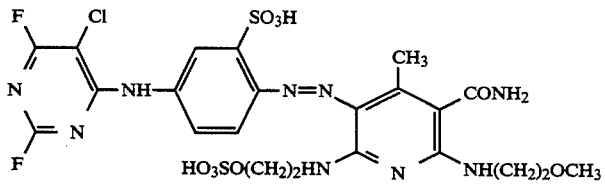 | Orange |

TABLE 2-continued
| Example | Reactive dye | Colour shade |
|---|---|---|
| 72 | 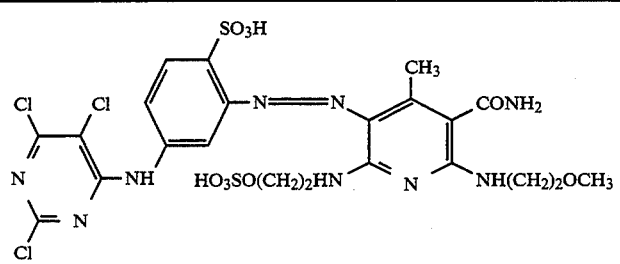 | Yellow |
| 73 | 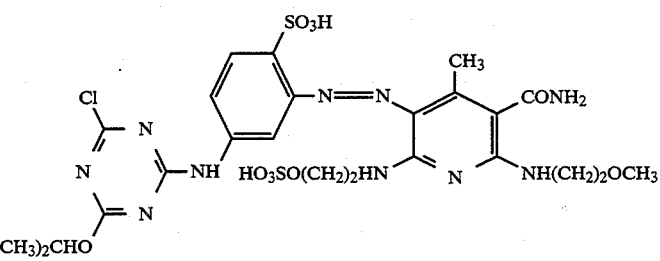 | Yellow |
| 74 | 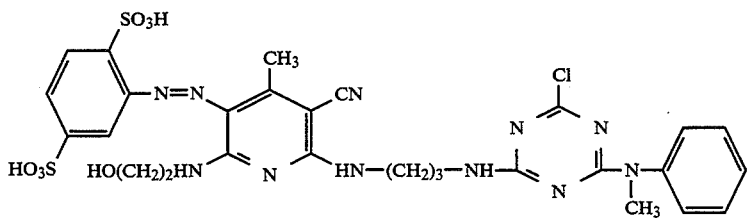 | Yellow |
| 75 | 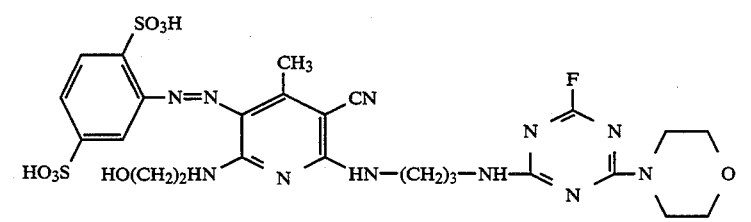 | Yellow |
| 76 | 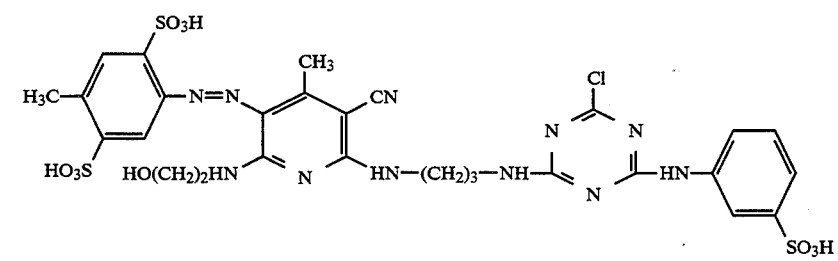 | Yellow |
| 77 | 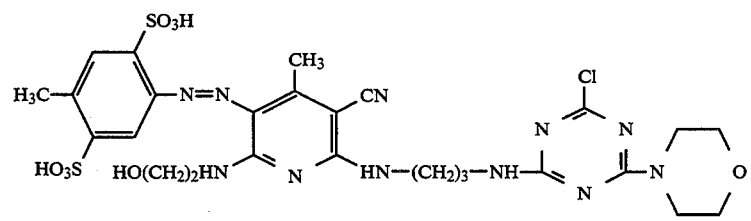 | Yellow |

TABLE 2-continued

| Example | Reactive dye | Colour shade |
|---|---|---|
| 78 | (structure) | Orange |
| 79 | (structure) | Orange |
| 80 | (structure) | Orange |
| 81 | (structure) | Orange |
| 82 | (structure) | Orange |
| 83 | (structure) | Orange |
| 84 | (structure) | Orange |

TABLE 2-continued

| Example | Reactive dye | Colour shade |
|---|---|---|
| 85 | | Orange |
| 86 | | Red |
| 87 | | Red |
| 88 | | Claret |
| 89 | | Claret |
| 90 | | Claret |

TABLE 2-continued

| Example | Reactive dye | Colour shade |
|---|---|---|
| 91 | (structure) | Claret |
| 92 | (structure) | Red |
| 93 | (structure) | Red |
| 94 | (structure) | Orange |
| 95 | (structure) | Orange |
| 96 | (structure) | Yellow |

TABLE 2-continued

| Example | Reactive dye | Colour shade |
|---|---|---|
| 97 | (structure) | Yellow |
| 98 | (structure) | Yellow |
| 99 | (structure) | Orange |
| 100 | (structure) | Orange |
| 101 | (structure) | Orange |
| 102 | (structure) | Yellow |
| 103 | (structure) | Yellow |

TABLE 2-continued

| Example | Reactive dye | Colour shade |
|---|---|---|
| 104 | Structure: 2-sulfophenyl-N=N-[pyridine with CH₃, CONH₂, HO₃SO(CH₂)₂NH substituents]-NH-(CH₂)₃-NH-C(=N-)-N=C(Cl)-N=C(morpholino) triazine | Yellow |
| 105 | Structure: 2-sulfophenyl-N=N-[pyridine with CH₃, CONH₂, HO₃SO(CH₂)₂NH]-NH-(CH₂)₃-NH-C(=N)-triazine(Cl)-NH-(3-sulfophenyl) | Yellow |
| 106 | Structure: 2-sulfophenyl-N=N-[pyridine with CH₃, CONH₂, HO₃SO(CH₂)₂NH]-NH-(CH₂)₃-NH-C(=N)-triazine(Cl)-NH-(3-NHCOCH₃-phenyl) | Yellow |
| 107 | Structure: 2-sulfophenyl-N=N-[pyridine with CH₃, CONH₂, HO₃SO(CH₂)₂NH]-NH-(CH₂)₃-NH-C(=N)-triazine(Cl)-NH(CH₂)₂SO₃H | Yellow |
| 108 | Structure: 2-sulfophenyl-N=N-[pyridine with CH₃, CONH₂, HO₃SO(CH₂)₂NH]-NH-(CH₂)₃-NH-C(=N)-triazine(F)-NH₂ | Yellow |
| 109 | Structure: 2-sulfophenyl-N=N-[pyridine with CH₃, CONH₂, HO₃SO(CH₂)₂NH]-NH-(CH₂)₃-NH-C(=N)-triazine(F)-NH(CH₂)₂OH | Yellow |
| 110 | Structure: 2-sulfophenyl-N=N-[pyridine with CH₃, CONH₂, HO₃SO(CH₂)₂NH]-NH-(CH₂)₃-NH-C(=N)-triazine(F)-NH(CH₂)₂O(CH₂)₂OH | Yellow |

TABLE 2-continued
| Example | Reactive dye | Colour shade |
|---|---|---|
| 111 | 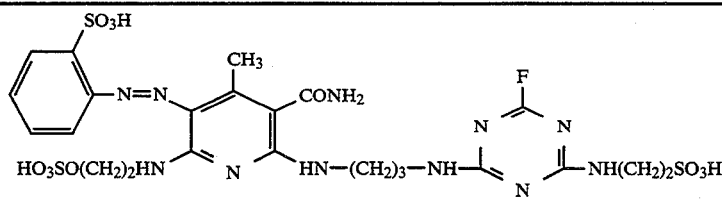 | Yellow |
| 112 | 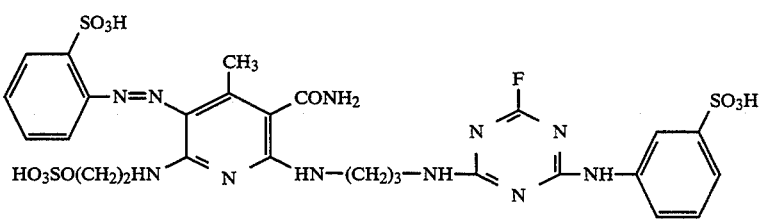 | Yellow |
| 113 | 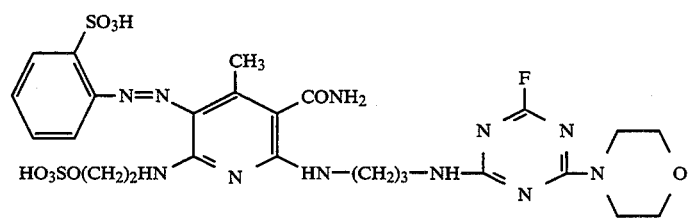 | Yellow |
| 114 | 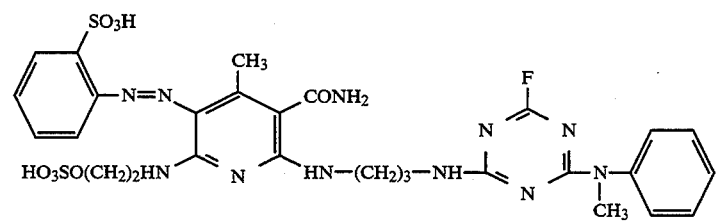 | Yellow |
| 115 | 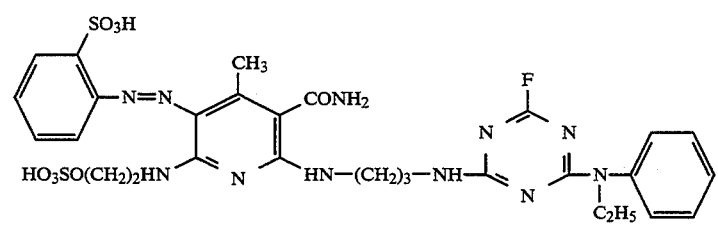 | Yellow |
| 116 | 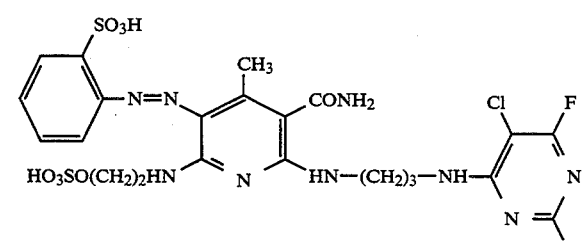 | Yellow |
| 117 | 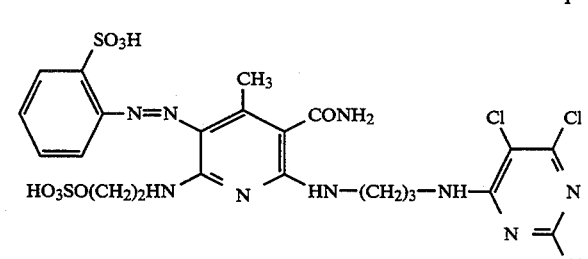 | Yellow |

TABLE 2-continued

| Example | Reactive dye | Colour shade |
|---|---|---|
| 118 | (structure) | Yellow |
| 119 | (structure) | Yellow |
| 120 | (structure) | Yellow |
| 121 | (structure) | Yellow |
| 122 | (structure) | Yellow |
| 123 | (structure) | Yellow |
| 124 | (structure) | Yellow |

TABLE 2-continued

| Example | Reactive dye | Colour shade |
|---|---|---|
| 125 | 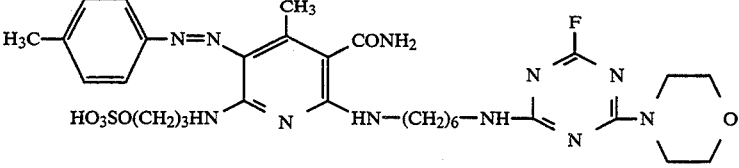 | Yellow |
| 126 | 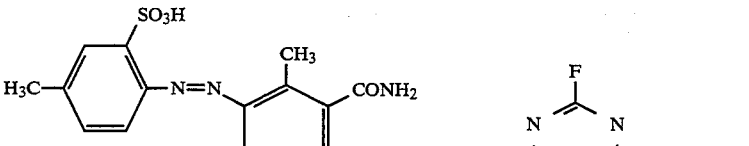 | Yellow |
| 127 | 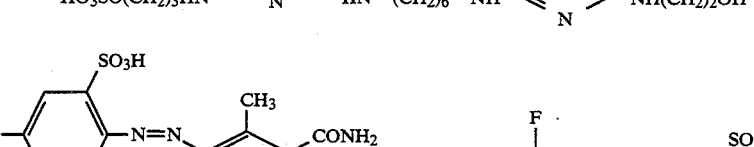 | Yellow |
| 128 | 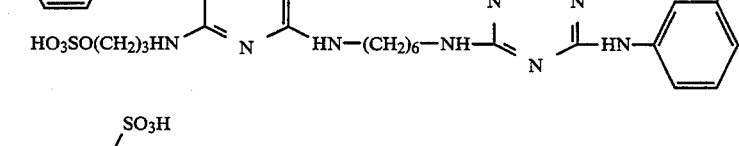 | Yellow |
| 129 | 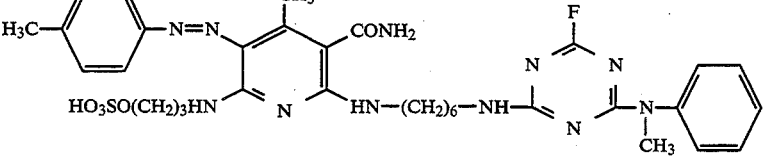 | Orange |

Dyeing instructions 2 parts of the reactive dye obtained according to Example 51 are dissolved in 400 parts of water; 1500 parts of a solution containing 53 g of sodium chloride per liter are added. 100 parts of cotton fabric are introduced into this dyebath. After 45 minutes, 100 parts of a solution which contains 16 g of sodium hydroxide and 20 g of calcined sodium carbonate per liter are added. The temperature of the dyebath is kept at 40° C. for a further 45 minutes. Thereafter, the dyed goods are rinsed, soaped at the boil with a non-ionic detergent for a quarter of an hour, rinsed again and dried.

Printing instructions 3 parts of the reactive dye obtained according to Example 51 are sprinkled into 100 parts of a stock thickener mixture comprising 50 parts of 5% sodium alginate thickener, 27.8 parts of water, 20 parts of urea, 1 part of sodium m-nitrobenzenesulfonate and 1.2 parts of sodium bicarbonate while stirring rapidly. A cotton fabric is printed with the printing paste thus obtained and is dried, and the resulting printed material is steamed in saturated steam at 102° C. for 2 minutes. The printed fabric is then rinsed, soaped at the boil, if appropriate, and rinsed again, and then dried.

What is claimed is:

1. A reactive dye of the formula

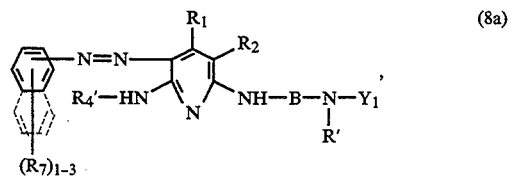

(8a)

-continued

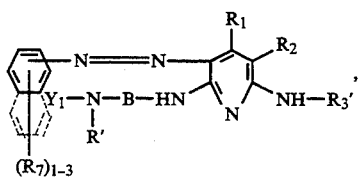  (8b)

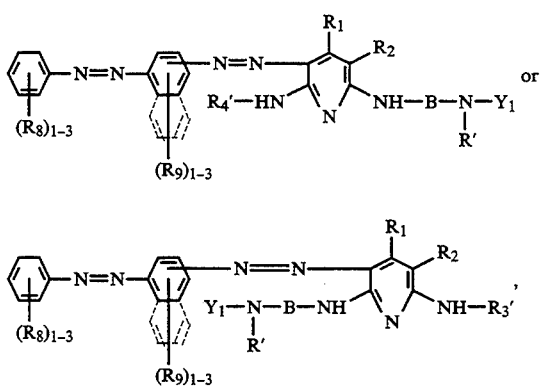

in which

R₁ is $C_1$–$C_4$alkyl,

R₂ is cyano, carbamoyl or sulfomethyl,

R', R₃' and R₄' independently of one another are hydrogen or $C_1$–$C_{12}$alkyl which is unsubstituted or substituted by hydroxyl, sulfo or sulfato and, with the exception of methyl, may be interrupted by oxygen, the radical —(NR')— can be a bivalent 5- to 7-membered aliphatic heterocyclic radical, $(R_7)_{1-3}$, $(R_8)_{1-3}$ and $(R_9)_{1-3}$ are in each case 1 to 3 identical or different substituents selected from the group consisting of hydrogen, $C_1$–$C_4$alkyl, $C_1$–$C_4$alkoxy, $C_2$–$C_4$alkanoylamino, halogen and sulfo, B is $C_2$–$C_{12}$alkylene which is unsubstituted or substituted by hydroxyl, sulfo or sulfato and may be interrupted by oxygen and Y₁ is a fibre-reactive radical of the formula

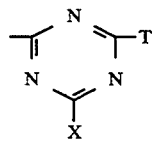  (6)

or

-continued

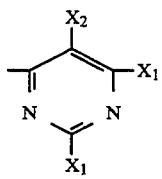  (7)

in which

X, X₁ and X₂ are halogen and

T is halogen, hydroxyl, sulfo, $C_1$–$C_4$alkoxy, $C_1$–$C_4$alkylthio, $C_1$–$C_4$alkylsulfonyl, phenylsulfonyl, morpholino or unsubstituted or substituted amino, and the reactive dyes of the formulae (8a), (8b), (9a) and (9b) each contain at least one permanent sulfo or sulfato group and only one fibre-reactive radical.

2. A reactive dye according to claim 1, wherein T is halogen; hydroxy; sulfo; $C_1$–$C_4$alkoxy; $C_1$–$C_4$alkylthio; $C_1$–$C_4$alkylsulfonyl; phenylsulfonyl; morpholino; amino; N—$C_1$–$C_4$alkylamino or N,N-di-$C_1$–$C_4$alkylamino each of which is unsubstituted or is substituted in the alkl radical by sulfo, sulfato, hydroxyl, carboxyl or phenyl; cyclohexylamino; or is N—$C_1$–$C_4$alkyl-N-phenylamino or phenylamino or naphthylamino each of which is unsubstituted or is substituted in the phenyl or naphthyl radical by $C_1$–$C_4$alkyl, $C_1$–$C_4$alkoxy, $C_2$–$C_4$alkanoylamino, carboxyl, sulfo or halogen.

3. A reactive dye according to claim 1, in which R₁ is methyl.

4. A reactive dye according to claim 1, in which R₂ is cyano or carbamoyl.

5. A reactive dye according to claim 1, in which B is $C_2$–$C_6$alkylene.

6. A reactive dye according to claim 1, in which a bivalent 5- to 7-membered aliphatic heterocyclic radical —(NR')— is a radical of the formula

7. A mixture of reactive dyes which comprises at least two reactive dyes of the formulae (8a), (8b), (9a) and (9b) according to claim 1.

8. A process for dyeing or printing fibre materials containing hydroxyl groups or nitrogen, which comprises the step of applying to the fibre material a tinctorial amount of a reactive dye according to claim 1.

9. A process according to claim 8 wherein the fibre material is cellulosic fibre material or naturally occurring or synthetic polyamide fibre material.

* * * * *